United States Patent

Newton et al.

[11] Patent Number: 6,008,662
[45] Date of Patent: Dec. 28, 1999

[54] APPARATUS AND METHOD FOR MEASURING CONDITIONS IN FLUIDIZED BEDS

[75] Inventors: Robert E. Newton, Tewksbury; David R. Day, Boxford; Ron L. Swartzentruber, Danvers, all of Mass.

[73] Assignee: Oxford Instruments America, Inc., Concord, Mass.

[21] Appl. No.: 08/741,917

[22] Filed: Oct. 31, 1996

[51] Int. Cl.$^6$ .................................................. G01R 27/00
[52] U.S. Cl. ........................ 324/724; 73/304 R; 324/713; 324/715
[58] Field of Search .......................... 73/304 R; 324/713, 324/715, 724

[56] References Cited

U.S. PATENT DOCUMENTS

| | | | |
|---|---|---|---|
| 4,373,113 | 2/1983 | Winkler et al. | 174/179 |
| 4,532,311 | 7/1985 | Fulks et al. | 526/62 |
| 4,792,592 | 12/1988 | Fulks et al. | 526/62 |
| 4,803,251 | 2/1989 | Goode et al. | 526/59 |
| 4,855,370 | 8/1989 | Chirillo et al. | 526/74 |
| 4,876,320 | 10/1989 | Fulks et al. | 526/62 |
| 5,391,657 | 2/1995 | Song et al. | 526/74 |
| 5,416,175 | 5/1995 | Song et al. | 526/74 |
| 5,428,118 | 6/1995 | Painter et al. | 526/74 |
| 5,648,581 | 7/1997 | Kubo et al. | 585/501 |

FOREIGN PATENT DOCUMENTS

0604990B1  7/1994  European Pat. Off. .

*Primary Examiner*—David W. Wu
*Attorney, Agent, or Firm*—Testa, Hurwitz & Thibeault, LLP

[57] ABSTRACT

Conditions in a fluidized bed are measured with a probe and a circuit. The bed can be a polymerization reactor's reaction chamber, and the conditions can result in "sheeting" which is the build up of polymer on the chamber walls. The probe protrudes into the bed and detects a current which generally is a function of at least the impact and charge of particulates in the bed. The current detected by the probe is related to the conditions in the bed. The circuit measures the detected current. The probe has an inner probe piece of metallic material within an insulator of polymeric material. A portion of the insulator protrudes a first distance into the bed, and a portion of the inner probe piece protrudes a second distance into the bed. The first distance is less than or equal to the second distance. The insulator typically does not extend as far into the bed as the inner probe piece.

7 Claims, 4 Drawing Sheets

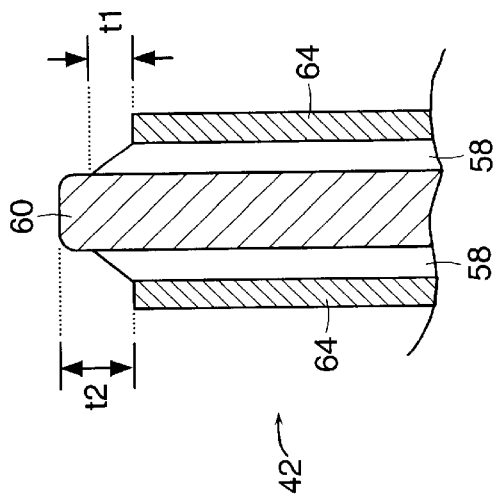
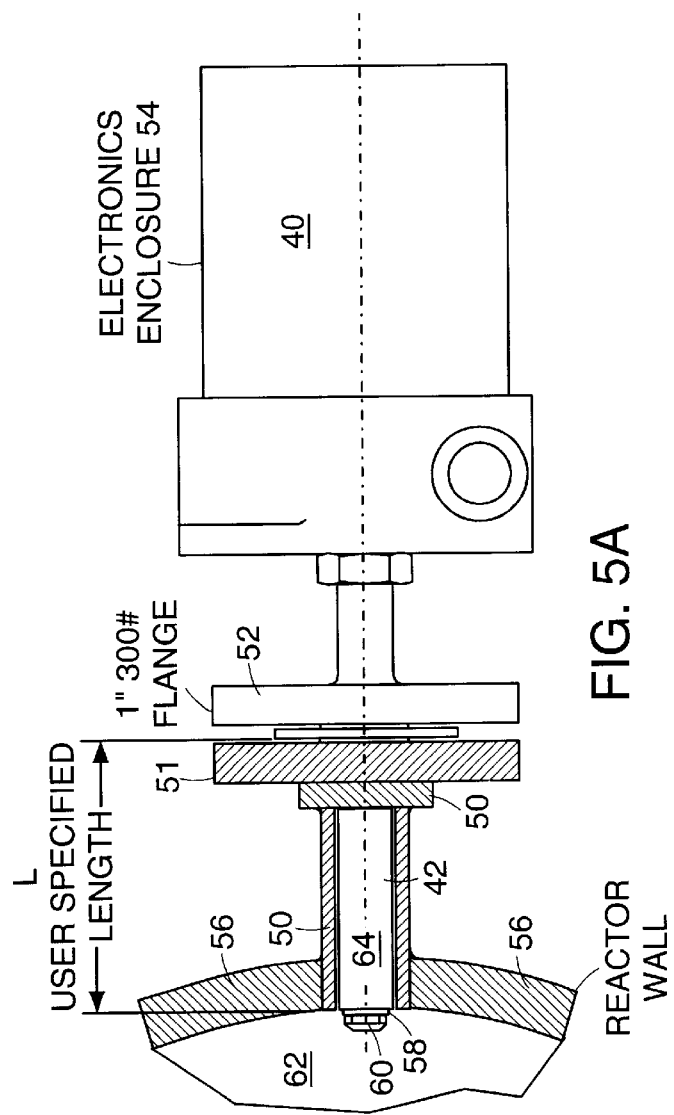

APPARATUS AND METHOD FOR MEASURING CONDITIONS IN FLUIDIZED BEDS

TECHNICAL FIELD

This invention relates to measuring conditions in fluidized beds such as the electrical conditions within a reaction chamber of a polymerization reactor.

BACKGROUND INFORMATION

"Sheeting" is known to occur in the reaction chamber of gas phase polymerization reactors. Sheeting is the adherence of fused catalyst and reactant particles to the walls of the reaction chamber. Sheeting generally is undesirable because it can disrupt temperature control of the reactor, can result in the creation of "chunks" of polymer material that fall off of the walls and clog a distribution plate (which maintains a gas stream for a fluidized bed in the reactor), and can result in the creation of "off-specification" polymer material that mixes with "on-specification" polymer material to provide an unacceptable batch of polymer material.

It is known to reduce sheeting during polymerization (i.e., polymer preparation) in a fluidized bed by introducing an additional substance to the materials used to create the polymer. The materials used to create the polymer typically are the reactant (e.g., a monomer) and the catalyst. The additional substance is introduced only to reduce sheeting. Additional substances that have been used to reduce sheeting are: charge-generating chemical additives such as magnesium oxide and vandium oxide; inert materials in particle or powder form such as silica; water; methanol; chromium-containing compounds; and "anti-stats" which are antistatic materials having a small amount of conductive material to aid in charge dissipation. Some of these substances, such as water and methanol, are known reaction poisons. It also is known to reduce sheeting during polymer preparation in a fluidized bed by introducing a tangential flow into the reaction chamber to remove build-up on the walls of the chamber.

Before sheeting is reduced in any of the ways mentioned in the preceding paragraph, it generally first must be detected. It is known to detect sheeting in a reaction chamber of a polymerization reactor by measuring the "static electricity" voltage in the reaction chamber with a fragile probe and a voltage divider circuit. The fragile probe generally is expensive to manufacture. It is believed, and generally described in the prior art, that high static voltages (e.g., 10 kilovolts or more) in the reaction chamber are indications of sheeting and/or other problems occurring or about to occur in the chamber. One end of the probe, which typically is a metal rod surrounded by a fragile insulating ceramic, protrudes into the reaction chamber and the other end of the probe connects to the circuit. The function of the circuit is to divide down most of the large voltage and thus allow a small voltage to be measured. The higher the voltage measured with the circuit, the higher the static voltage in the reaction chamber and the more sheeting in the reaction chamber that may result.

It also is known to use the fragile probe and voltage divider circuit combination described above to measure the static electricity voltage in fluidized beds generally. High voltages in a fluidized bed are believed to cause, or contribute to, problems with the functioning of the bed and problems with the material being mixed or created with the bed. Fluidized beds are used in a variety of industries including pharmaceutical, food, and metal to mix and react substances and make various drugs, foods, and other products.

Because it is believed that high static voltages are possible in the fluidized beds, the insulator used for the probe is a high quality insulating material, such as ceramic which is expensive and fragile and thus prone to breakage, to prevent arcing from the probe to ground. Also, because of the high static voltages, special safety equipment must be used such as a grounding bar outside the reactor to prevent accidental shocks to anyone making a connection to the reactor and to prevent sparks or arcing which might result in an explosion of various substances in the vicinity and atmosphere near these reactors. It is typical to have ignitable or explosive substances (e.g., gases, chemicals, etc.) near the reactor.

A way is needed to detect problems in fluidized beds (e.g., sheeting in a reaction chamber of a polymerization reactor) without using expensive-to-manufacture, fragile insulating materials such as ceramics on the probe and without the need for special safety equipment such as grounding bars and spark protectors.

SUMMARY OF THE INVENTION

It has been discovered that the high voltage levels measured by known methods using a probe and a voltage divider circuit are primarily determined by the circuit itself and not necessarily the conditions (e.g., sheeting) in the reaction chamber of the polymerization reactor. That is, the magnitude of the potential is an artifact of the measurement circuit utilized to measure the potential. It has been discovered that the probe potential depends on the total resistance of the known voltage divider circuit, and that the current through the circuit is nearly constant for a given period of time regardless of the total resistance of the circuit. Because the current through the measuring circuit is nearly constant for a given time period independent of the total resistance of the circuit, it is possible to use a new, simpler, and more robust measuring probe and circuit. In brief, it has been discovered that the current is actually the important and reproducible quantity to be measured and not the voltage.

From this discovery, flows the realization that, to measure conditions in fluidized beds, the current should be measured instead of the voltage, and a low-resistance measuring circuit can be used to measure that current. When the new low-resistance circuit is used, much lower probe tip voltages are achieved. Along with the disappearance of the high voltages is the disappearance of the need for special high-voltage probe insulating material and related high-voltage safety precautions. The probe can now be designed for mechanical strength instead of resistance to electrical breakdown. For example, the probe can use non-ceramic insulating materials such as an epoxy-glass composites, kevlar, polyimide, polyamide, phenolic, teflon, and polyetheretherketone (PEEK) fluorinated polymer or other fluorinated materials. In general, any high-strength polymeric material can be used in place of the fragile ceramic insulator used in the prior art.

It is an object of the invention to measure the conditions in a fluidized bed (e.g., the reaction chamber of a gas phase polymerization reactor) by measuring the current generated by a probe protruding into the bed instead of measuring the voltage.

It is another object of the invention to eliminate the need for high quality, expensive, fragile probe insulating material such as ceramic.

It also is an object to eliminate the need for various safety equipment such as a grounding bar and the need for special precautions against sparking and arcing.

In general, the invention involves measuring conditions in a fluidized bed (e.g., a reaction chamber of a polymerization reactor) by detecting a current related to the conditions in the bed and measuring the current. A probe is used to detect the current. The probe preferably protrudes into the bed, and the current generally is a function of at least the impact on the probe of particulates in the bed and the charge of the particulates. A circuit measures the current from the probe, and preferably measures magnitude, polarity, and change in the polarity of the current. The probe comprises an inner probe piece of metallic material within an insulator of polymeric material. An outer probe sheath of metallic material typically also is provided, wherein the insulator is within the outer probe sheath and the inner probe piece is within the insulator. A portion of the insulator extends beyond a distal end of the outer probe sheath to allow that portion of the insulator to protrude a first distance into the bed. A portion of the inner probe piece extends beyond the distal end of the outer probe sheath and a distal end of the insulator to allow that portion of the inner probe piece to protrude a second distance into the bed. The first distance is less than or equal to the second distance. The first distance typically is less than the second distance such that, when the probe is inserted into the bed, the inner probe piece extends further into the bed than the surrounding insulator.

The first distance preferably is less than 20 mm. The circuit preferably has a bandwidth of about 100 Hertz. The polymeric material of the insulator preferably is a high-strength polymeric material such as an epoxy-glass composite, kevlar, polyimide, polyamide, phenolic, teflon, or PEEK fluorinated polymer or other fluorinated material.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 5A is a diagram of a device according to the invention, including a probe and a circuit shown coupled to a fluidized bed.

FIG. 5B is a diagram in cross section of a portion of the probe of FIG. 5A.

DESCRIPTION

Figure 1:
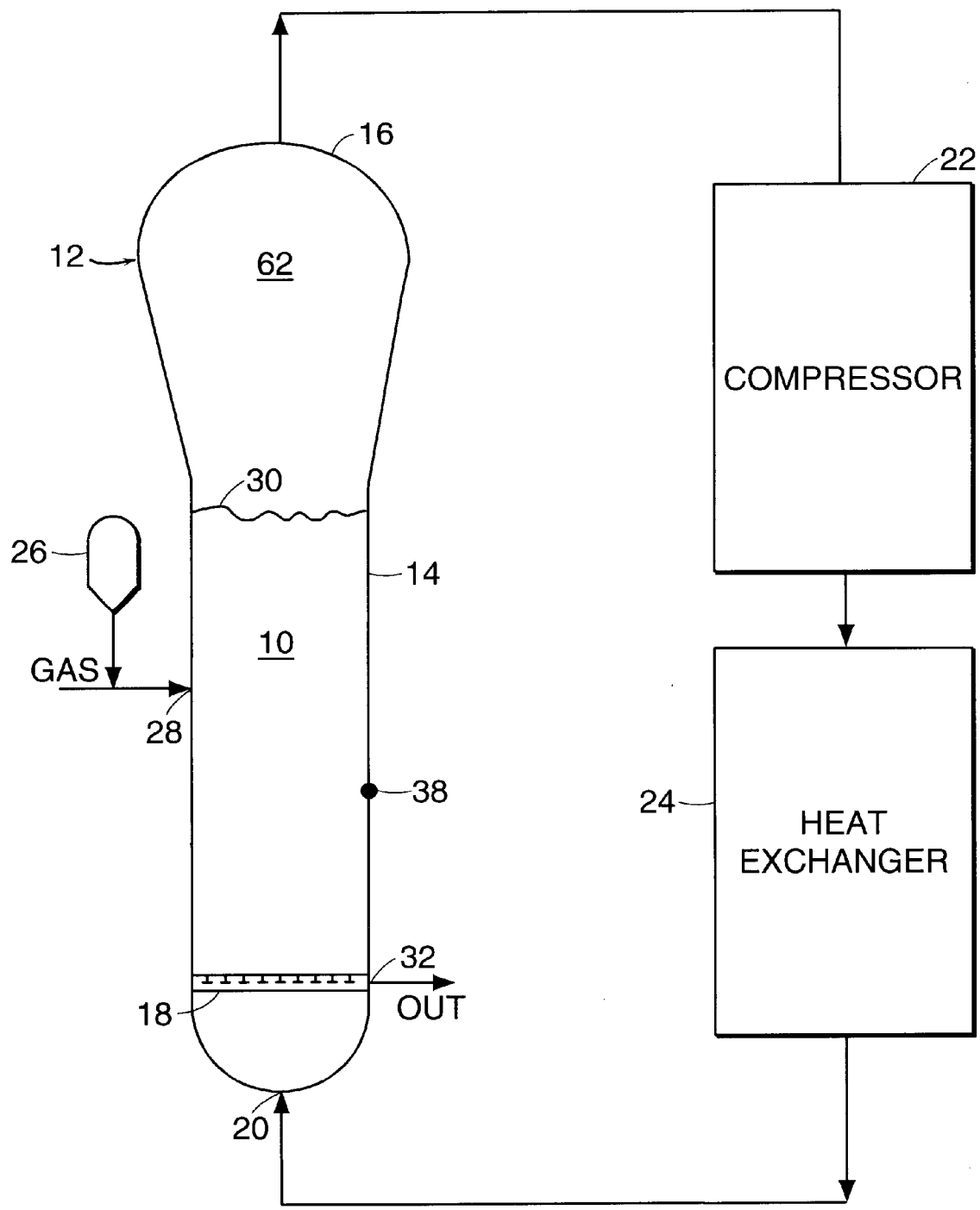
FIG. 1 is a diagram of a fluidized bed which can be used, for example, as a reaction chamber of a polymerization reactor, the fluidized bed being the environment generally in which the invention operates.

Referring to FIG. 1, the invention relates to the measurement of conditions in a fluidized bed 10. In some preferred embodiments, contained within a reaction chamber 62 of a polymerization reactor such as a gas phase polymerization reactor 12 which polymerizes alpha-olefins, and the conditions of interest are those that result in the build-up of polymer on walls of the chamber (i.e., sheeting). While a single fluidized bed 10 is shown, it is possible to utilize the invention in a multiple (i.e., staged) bed environment in which the conditions in one or more of the beds are measured according to the invention. The invention has general applicability to fluidized beds, regardless of what is being mixed or reacted in or by the bed(s). The bed 10 can be used in the making of various drugs, foods, and other products in the pharmaceutical, food, metal, and other industries.

A brief description is now provided of the fluidized bed 10 and the environment generally in which the invention operates. The bed includes a reaction zone or straight section 14 and a velocity reduction zone or expanded section 16. In the case of the polymerization reactor 12, the reaction zone 14 of the bed/reaction chamber 10 includes growing polymer particles, formed polymer particles, and some amount of catalyst particles which are fluidized by the continuous flow of cycle fluidizing gas. The fluidizing gas is supplied to a distribution plate 18 through an inlet 20 at the base of the bed 10. The portion of the fluidizing gas not reacting in the reaction zone 14 constitutes recycle gas which passes through the expanded section 16 and is compressed by a compressor 22. The compressed recycle gas then passes through a heat exchanger 24 where it is stripped of heat before it is returned to the reaction zone 14. Catalyst from a reservoir 26 typically is injected into the bed 10 (generally at a rate equal to its consumption) at a point 28 above the distribution plate 18 by using an inert gas such as nitrogen or argon to carry the catalyst into the bed 10. The material in the reaction zone 14 is maintained at about a constant height 30 by withdrawing (typically at a point 32 near the distribution plate 18) some of the material at a rate equal to the polymer product formation rate. The withdrawn material is the polymer product formed by the bed 10. The operation of gas phase polymerization reactors 12 and fluidized beds generally is well known, and thus it is not described here in further detail.

Figure 2:
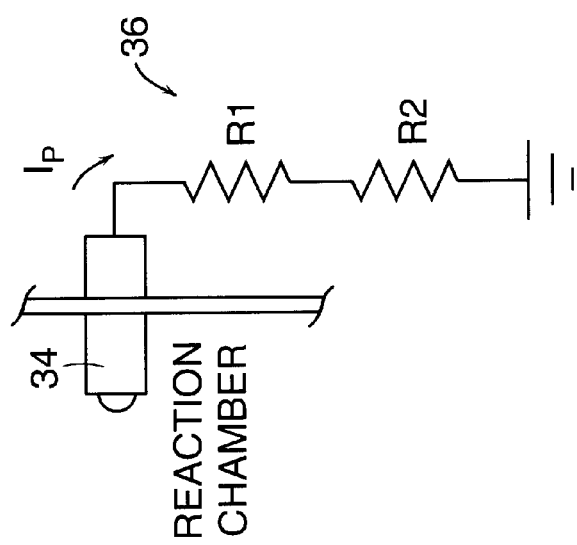
FIG. 2 is a diagram of a traditional electrostatic probe and measuring circuit configuration.

Referring to FIGS. 1 and 2, it is generally believed that high static voltages (e.g., 10 kilovolts or more) in the reaction chamber 62 of a gas phase polymerization reactor 12 are indications of sheeting and/or other problems in the chamber, and it is known to measure such voltages with a probe 34 and a voltage divider circuit 36. The probe 34 typically protrudes into the reaction zone 14 at a point 38 somewhere above the distribution plate 18, and typically has a metal rod surrounded by a fragile, expensive, insulating ceramic material. The circuit 36 is designed to divide down most of the expected high static voltage with R1, thereby allowing a small voltage to be measured across R2. For example, a probe tip voltage of 1200 Volts and a voltage across R2 of about 3 millivolts is not uncommon.

It is generally believed that the higher the voltage measured across R2, the higher the static voltage in the reaction chamber and the more sheeting and/or other problems therein. A high voltage in the chamber is believed to be an indication of problems generally in the chamber, not just the problem of sheeting. Because of the expected high voltages, the high quality insulating ceramic is used for the probe 34 to prevent arcing from the probe 34 to ground. Also, it is known to use special safety equipment (e.g., grounding bar outside the reactor to prevent accidental shocks to anyone making a connection to the reactor, and various precautions to prevent sparks or arcing which might result in an explosion of various substances in the vicinity and atmosphere near these reactors) because of the expected high voltages.

The invention allows detection of conditions in fluidized beds (e.g., sheeting in a reaction chamber of a polymerization reactor) without the use of expensive, fragile insulating material such as ceramic on the protruding probe and without the need for special safety equipment such as grounding bars and spark/arc protectors.

Figure 3:
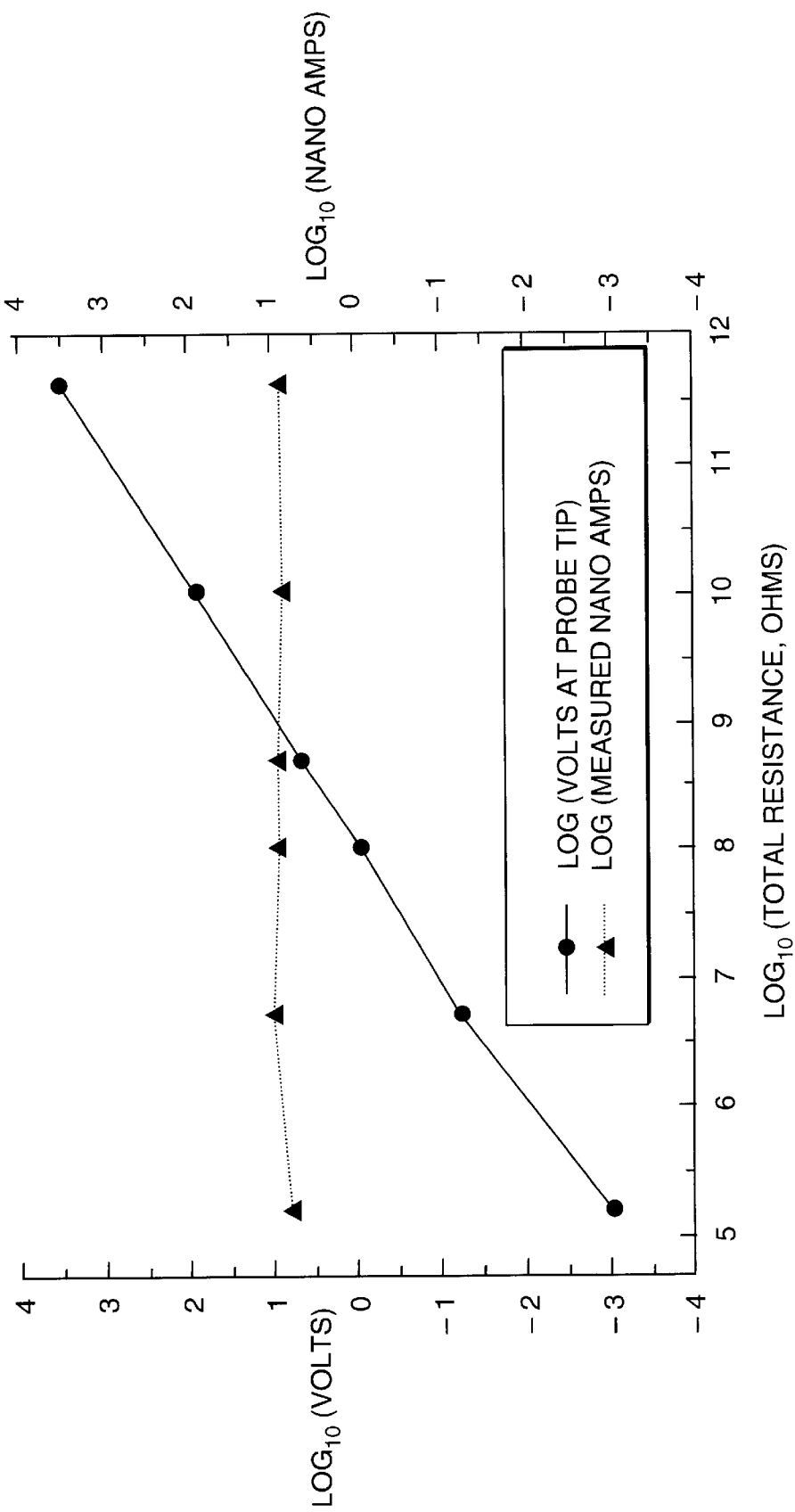
FIG. 3 is a graph of potential versus total resistance, and current versus total resistance, for traditional electrostatic probe and measuring circuit configurations such as the traditional configuration of FIG. 2.

It has been discovered that the high voltage levels measured by known probe/voltage divider circuit configurations are primarily determined by the circuit itself and not necessarily the conditions in the reaction chamber of the reactor. Referring to FIG. 3, for a given period of time, the measured potential varies with the total resistance (R1+R2) of the known voltage divider circuit 36, and the current through the circuit 36 is nearly constant regardless of the total resistance (R1+R2) of the circuit 36. The period of time over which the data is shown in the graph of FIG. 3 is 30 minutes.

These discoveries resulted in the realization that it is possible to remove R1 (the larger-value resistor) from the traditional voltage divider circuit 36 and the current through R2 (the smaller-value resistor) will remain the same. The current, and not the traditionally-measured voltage, is the more important and reproducible quantity that should be measured, and it is not necessary to use a large "voltage dropping" resistor like R1 in order to make the desired measurement. R1 might be eliminated entirely (i.e., R1=0), and the voltage reading across R2 should not change because the current through the circuit 36 (i.e., through the two series resistors R1 and R2) is constant.

To measure the current instead of the voltage in accordance with the invention, a low-resistance (relative to the total resistance of the traditional voltage divider circuit) current-measuring circuit is used. With the low-resistance currentmeasuring circuit of the invention, much lower probe tip voltages are measured as compared to the probe tip voltages measured with the traditional voltage divider circuit 36. Because of the disappearance of the high voltages, the need for special high-voltage probe insulating material like ceramic and safety precautions/equipment is eliminated in accordance with the invention. The probe can now be designed for mechanical strength instead of resistance to electrical breakdowvn. For example, a probe can be used which does not use ceramic as the insulating material.

Figure 4:
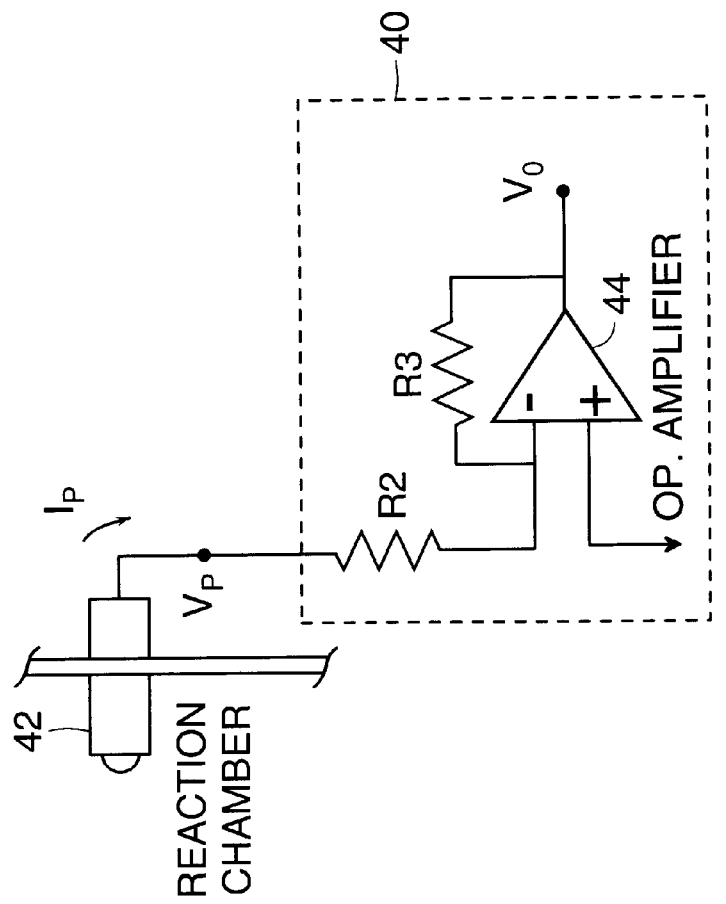
FIG. 4 is a diagram of an embodiment of a probe and a current-measuring circuit according to the invention.

Referring, to FIG. 4, a presently preferred embodiment of the invention includes a current-measuring circuit 40 (dotted box) and a probe 42 that uses an epoxy/glass composite which is an insulating material that is less fragile and less expensive as compared to the ceramic used with the traditional probe 34. In general, and according to the invention, any high-strength polymeric material can be used as the insulator in the probe 42. Examples of possible polymeric materials, in addition to an epoxy-glass composite, include kevlar, polyimide, polyamide, phenolic, teflon, polyetheretherketone (PEEK) fluorinated polymer, fluorinated materials, and the like. In one embodiment, the circuit 40 comprises an "inverting amplifier" which has two resistors R2, R3 and an operational amplifier 44 and which is governed by $$V_o = -(R3 * I_p) = -((R3/R2) * V_p).$$

In this disclosed embodiment, R2 of the circuit 40 is about 100 kilohms ($100 \times 10^3 \Omega$) to about one megohm ($1 \times 10^6 \Omega$). The value of R3 can be selected to make $V_o$ fall within a desirable range. For example, if R3=100 k$\Omega$ and $I_p$=3 nanoamps, $V_o$ would have a magnitude of about 0.3 millivolts. Other current-measuring circuits 40 are possible besides the disclosed inverting amplifier, and one of ordinary skill will be able to construct such circuits.

The current, $I_p$, that is detected by the probe 42 and measured by the circuit 40 is a function of at least two things, the impact on the probe 42 of particles in the bed (e.g., the polymer particles and the catalyst particles) and the charge of the particles in the bed. In general, the current, $I_p$, results from: (i) neutral particles hitting the probe 42 (the traditional triboelectric effect); (ii) charged particles hitting the probe 42; and (iii) charged particles that do not physically impact the probe 42 but come close enough to create an AC pulse on the probe 42. $I_p$ is the current graphed in FIG. 3.

Sheeting in a fluidized bed generally is preceded by an increase of positive and negative going signals and the associated amplitudes. These signals may be on the order of tens of Hertz, and thus impossible to measure with traditional measuring circuits, like the circuit 34 in FIG. 2, that have very low bandwidths such as less than 10 Hz bandwidth.

In accordance with the invention, the circuit 40 measures the magnitude and the polarity of $I_p$. Change in polarity of $I_p$ also is an important measurement which is made by the circuit 40. In general, $I_p$ is related to the conditions in the reaction chamber, and measuring it gives an indication of those conditions. Also, circuits according to the invention, such as the circuit 40, are capable of maintaining high gain (up to 0.1 nanoamps full scale) with a bandwidth of 100 Hertz. This enables measurement of both the longer term DC characteristics as well as AC responses up to 100 Hertz characteristics of pre-sheeting conditions.

Referring to FIGS. 5A and 5B, in one embodiment, the probe 42 is provided within a metal (e.g., carbon steel or stainless steel) housing 50. The metal housing 50 together with a flange 51 has a user-specified length, L. The flange 51, which is at ground potential as are the housing 50 and the reactor wall 56, mates via another flange 52 with an electronics enclosure 54 within which is the circuit 40. The housing 50 fits into an opening in the reactor wall 56 and allows an insulator 58 and an inner probe piece 60 of the probe 42 to protrude into the reaction chamber 62 and the fluidized bed. The insulator 58, which is made of a high-strength polymeric material such as the epoxy-glass composite or other polymeric materials mentioned above to provide high strength and impact absorbency, extends a distance, t1, into the reaction chamber 62 which is less than 20 mm, preferably less than 12 mm all the way down to about 0.5 mm of exterision, in accordance with the invention. In traditional probe designs with ceramic insulators, a larger amount of insulator must be exposed in the reaction chamber 62, typically at least about 20 mm, to roduce the risk of arcing to the reactor wall from the exposed inner probe piece 60. This large exposure of insulator in prior probe designs increases the likelihood of probe breakage because more insulator is showing and ceramic is brittle. The inner probe piece 60, which is made of a metallic material such as carbon steel or stainless steel, extends a further distance, t2, into the reaction chamber 62. The distance, t2, typically ranges from about 0.5 mm to 50 mm. The invention thus involves the use of a minimally-exposed insulator 58 which allows more metal shielding and stronger probes than heretofore known that can withstand impacts from, for example, any chunks inside the bed 10. Around the insulator 58 typically is an outer probe sheath 64 made of a metallic material such as carbon steel or stainless steel. The sheath 64, like the reactor wall 56 and the housing 50, is at ground potential. In this embodiment, the inner probe piece 60 is a solid metal rod, the insulator 58 is a tubular sleeve around the piece 60, and the outer sheath 64 is another tubular sleeve around the insulator 58.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. Apparatus for measuring electrical conditions in a fluidized bed, the apparatus comprising:

a probe for detecting a current related to the electrical conditions in the bed, the probe comprising an inner probe piece of metallic material within an insulator of polymeric material, a portion of the insulator for protruding a first distance into the bed, a portion of the inner probe piece for protruding a second distance into the bed, the first distance being less than or equal to the second distance; and a circuit for measuring the current.

2. The apparatus of claim 1 wherein the current is a function of at least impact on the inner probe piece of particles in the bed and charge of the particles in the bed.

3. The apparatus of claim 1 wherein the circuit measures magnitude of the current, polarity of the current, and change in the polarity of the current, and the circuit has a bandwidth of about 100 Hertz.

4. The apparatus of claim 1 wherein the fluidized bed is in a reaction chamber of a polymerization reactor and wherein the electrical conditions result in build-up of polymer on walls of the reaction chamber.

5. The apparatus of claim 1 wherein the first distance is less than 20 mm.

6. The apparatus of claim 1 wherein the polymeric material of the insulator comprises an epoxy-glass composite material.

7. The apparatus of claim 1 wherein the probe further comprises an outer probe sheath of metallic material, the insulator being within the outer probe sheath and the inner probe piece being within the insulator.

* * * * *